Figure 1:
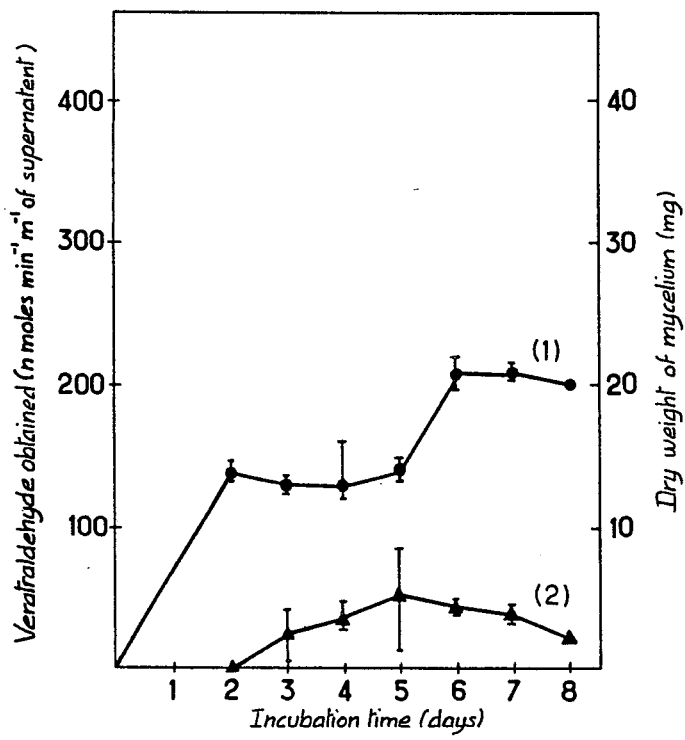

United States Patent [19]

Buswell et al.

[11] Patent Number: 4,889,807
[45] Date of Patent: Dec. 26, 1989

[54] **MICROORGANISMS OF THE *PHANEROCHAETE CHRYSOSPORIUM* STRAIN AND THEIR USE**

[75] Inventors: John A. Buswell, Paisley, Scotland; Etienne Odier, Paris, France

[73] Assignee: Institut National de la Recherche Aronomique, France

[21] Appl. No.: 807,253

[22] Filed: Dec. 10, 1985

[30] Foreign Application Priority Data

Dec. 12, 1984 [FR] France ................................ 84 19028

[51] Int. Cl.$^4$ .......................... C12N 9/08; C12N 9/02; C12N 1/14
[52] U.S. Cl. ..................................... 435/192; 435/189; 435/254; 435/277; 435/278
[58] Field of Search ............... 435/189, 195, 196, 254, 435/192, 278, 277, 911

[56] References Cited

U.S. PATENT DOCUMENTS 4,554,075 11/1985 Chang et al. ........................ 435/262

OTHER PUBLICATIONS

Applied and Environmental Microbiology, vol. 42, No. 2, pp. 290–292 (Aug. 1981).
Science, vol. 221, pp. 661–663 (Aug. 1983).
Proceedings National Academy of Science, vol. 81, pp. 2280–2284 (Apr. 1984).
Journal of Bacteriology, vol. 135, pp. 790–797 (1978).
ATCC Catalogue of Fungi/Yeasts, 16th edition, 1984, p. 221.
Buswell, J. A. et al., (1984), Fems Microbiol. Lett., 25, 295–299.

*Primary Examiner*—Thomas G. Wiseman
*Assistant Examiner*—Charles L. Patterson
*Attorney, Agent, or Firm*—Brumbaugh, Graves, Donohue & Raymond

[57] ABSTRACT

The invention relates to new microorganisms of the *Phanerochaete chrysosporium* strain, which are useful especially for the production of lignin-degrading enzyme.

These new microorganisms are deposited under nos. C.N.C.M.-I-398 and C.N.C.M.-I-399.

20 Claims, 2 Drawing Sheets

MICROORGANISMS OF THE *PHANEROCHAETE CHRYSOSPORIUM* STRAIN AND THEIR USE

The present invention relates to new microorganisms of the *Phanerochaete chrysosporium* strain and to their use for the production of lignin-degrading enzyme.

The biodegradation of lignin plays an essential part in the terrestrial carbon cycle.

After cellulose, this compound represents the most abundant organic material capable of renewing itself. It also has the ability to become incrusted and, until it decomposes, to prevent degrading bacteria from gaining access to the cellulose and hemicelluloses of the tissues of ligneous plants.

The Basidiomycetes fungi, which cause white rot in wood, are capable of degrading all the constituents of the plant wall, including the lignin. The degradation of this phenolic polymer has been studied more particularly on the fungus *Phanerochaete chrysosporium*.

This fungus and other species causing the white rot in question are consequently capable of being applied in a variety of fields such as wood and paper technology and the production of chemical compounds from lignocellulose waste.

Nevertheless, the range of such potential applications could be widened if methods were available for selecting strains of greater capacities.

Various studies on the nutritional regulation of the degradation of lignin by the fungus *Phanerochaete chrysosporium* have established a clear relationship between a nitrogen deficiency in the culture medium and the appearance of lignin-degrading activity.

For example, *P. chrysosporium* ME-446 (ATCC 34541) degrades lignin not during its active growth phase but during the stationary phase when it is nutritionally deficient.

The degradation of lignin by this fungus consequently represents a characteristic of a secondary metabolism, the influence of nitrogen playing a part in establishing and maintaining this lignin-degrading activity.

Also, in J. of Bacteriology, Sept. 1978, pages 790–797, Keyser et al. have shown that the decomposition of lignin by *P. chrysosporium* takes place to a significant extent only when the culture medium is deficient in nitrogen.

The intensity of the repression of the lignin-degrading system by nitrogen varies according to the chosen nitrogen source. Glutamic acid is a powerful repressor of lignin degradation and, together with glutamine, seems to play a preferential part in the regulation of lignin-degrading activity [FENN et al., Arch. Microbiol. 130, pages 59–65 (1981)].

With other microorganisms, a secondary metabolism is activated under the influence of various nutritional deficiencies.

In the case of *P. chrysosporium*, the lignin-degrading system can also be stimulated under the influence of a carbohydrate and sulfur deficiency in the culture medium, although it has been considered that a nitrogen deficiency alone is necessary for obtaining substantial lignin degradation (Jeffries et al., Applied and Environmental Microbiology, Aug. 1981, pages 290–296).

In Science 221, pages 661–663 (1983), Ming Tien and T. Kent Kirk have reported the discovery of an extracellular enzyme produced by *Phanerochaete chrysosporium* Burdsall, this enzyme being capable, in the presence of hydrogen peroxide, of causing the oxidative degradation of different model compounds having the substructure of lignin, as well as the degradation of lignin from the fir tree or birch tree.

This enzyme, produced by *P. chrysosporium* BKM-1767 (ATCC 24725) or by *P. chrysosporium* ME-446 (ATCC 34541), has been described in Proc. Natl. Acad. Sci. U.S.A., volume 81, pages 2280–2284 (1984) as being a glycoprotein of about 42,000 daltons, containing one protoheme IX per molecule. In a non-stereospecific fashion, it catalyzes several oxidations in the alkyl side-chains of molecular models of the lignin type (monomers or dimers) or of macromolecular lignins: $C_{60}$–$C_{62}$ cleavage in compounds of the type aryl-$C_\alpha$—HOH—$C_\beta$HR—$C_\alpha$H$_2$O (R=aryl or O-aryl), oxidation of benzyl alcohols to aldehydes or ketones, intradiol cleavage of phenylglycol structures, and hydroxylation of the methylene radical of benzyl groups. The enzyme in question also catalyzes the oxidative coupling of phenols, probably explaining the relationship which has long been known between phenol oxidation and lignin degradation.

All these reactions require the presence of hydrogen peroxide in order to proceed.

This enzyme constitutes a unique oxygenase due to the fact that its activity cannot be exerted without hydrogen peroxide.

For reasons of convenience, the enzyme described in this way will hereafter be referred to as "lignin-degrading enzyme".

Control of the production conditions of this enzyme is still poor, however, and the slowness of the lignin biodegradation process constitutes a limiting factor in the applications currently envisaged: the enzymatic or microbial delignification of agricultural or forestry by-products for the purpose of improving their digestibility for ruminants, enzymatic hydrolysis of the cellulose or an anaerobic fermentation.

Consequently, it would be a major asset for future industrial applications to be able to obtain hyperactive lignin-degrading strains of *P. chrysosporium* capable of disturbing the lignin-degrading system.

It has now been found, surprisingly, that, in media containing unlimited nitrogen, microorganisms of the *Phanerochaete chrysosporium* strain are capable of developing a much greater lignin-degrading activity than the known *P. chrysosporium* strains, the operating conditions consequently being more advantageous than those required by the prior art.

Thus, the invention relates firstly to two new microorganisms of the species *Phanerochaete chrysosporium* Burdsall.

The invention also relates to the use of the new *Phanerochaete chrysosporium* microorganisms according to the invention for the production of lignin-degrading enzyme.

The microorganisms according to the invention are deposited at the Institut Pasteur (Paris) in the Collection Nationale de Cultues de Microorganismes (C.N.C.M.) (National Collection of Microorganism Cultures) under the respective numbers I-398 and I-399.

The invention further relates to a process for the production of a culture supernatant containing lignin-degrading enzyme, which process comprises cultivating the new *Phanerochaete chrysosporium* microorganisms of the invention in a nutrient medium which is not deficient in a source of assimilable nitrogen and which contains a source of assimilable carbon and assimilable mineral salts.

Likewise, the invention relates to a process for the production of lignin-degrading enzyme, which process comprises cultivating the new *Phanerochaete chrysosporium* microorganisms of the invention in a nutrient medium which is not deficient in a source of assimilable nitrogen and which contains a source of assimilable carbon and assimilable mineral salts, to give a culture supernatant containing lignin-degrading enzyme, which is isolated, for example, by means of centrifugation, dialysis and chromatography techniques.

According to an embodiment for the production of a supernatant containing the lignin-degrading enzyme in question, a plant inoculum is prepared by inoculating a small quantity of the culture medium with a conidial suspension of the microorganism.

This microorganism is then cultivated under conditions of aerobiosis, or preferably under oxygen, at a temperature of between 28° C. and 40° C., preferably at 37° C., and on different nutrient media containing a nitrogen source, a carbon source and mineral salts.

Before inoculation with the microorganism, it is desirable to adjust the pH of the culture medium to 4.5–5. This is done using a sodium 2,2'-dimethylsuccinate buffer adjusted with an alkali metal hydroxide, for example potassium hydroxide.

In general, there is a significant production of lignin-degrading enzyme within the supernatant from day 3 to day 8 with a maximum on day 5 or 6.

Examples of sources of assimilable carbon used are glucose, mannose, starch, melibiose, mannitol, xylose, maltose, adonitol, arabitol, fructose, sorbitol, raffinose, xylitol, D(+)-trehalose or glycerol.

Examples of possible sources of assimilable nitrogen are asparagine, ammonium nitrate or ammonium tartarate.

Examples of possible mineral salts are iron citrate, $KH_2PO_4$, $ZnSO_4$, $MnSO_4$, $CaCl_2$, $CuSO_4$, NaCl, $FeSO_4$, $CoCO_4$, $ZnSO_4$, $AlK(SO_4)_2$, $H_3BO_3$, $Na_2MoO_4$ or $MgSO_4$.

Glycerol is the preferred carbon source according to the invention. It has in fact been noted that this nutrient source in a medium which is not deficient in nitrogen makes it possible to obtain extremely high levels of ligninase or even lignin-degrading activity, unlike the strains *P. chrysosporium* BKM-1767 (ATCC 24725) and ME-446 (ATCC 34541), which do not produce lignin-degrading enzyme under these conditions.

As reported previously, a deficiency of nitrogen and carbon in the culture medium represents a necessary condition for the appearance of significant lignin-degrading activity among all the strains of *P. chrysosporium* examined hitherto.

Thus, the culture of the microorganisms according to the invention is media which are not deficient in nitrogen or glycerol would make it possible to obtain the lignin-degrading activity in question in a continuous process, which could not be envisaged with the known strains of *P. chrysosporium* since it is necessary in this case continuously to adjust the culture medium in order to comply with the nutritional deficiencies.

The lignin-degrading enzyme contained in the supernatants of the cultures of the microorganisms according to the invention can be isolated in particular by centrifugation, dialysis and chromatography, for example by chromatography on a column of agarose gel.

The enzyme obtained in this way can then be stored after lyophilization.

Cultures of the new microorganisms were prepared for the purpose of studying the enzyme or ligninase activity, the lignin-degrading activity and also a variety of parameters such as the influence of the carbon and nitrogen sources on the growth of the mycelium or on the enzyme activity.

I. Growth of the mycelium

The general procedure described in the example below was used here, the quality of the carbon source and/or the nitrogen content (asparagine/$NH_4NO_3$) of the nutrient medium being varied, and the dry weights of the mycelia were determined, after isolation and drying, by means of glass fiber filters 2.5 mm in diameter.

Figure 2:
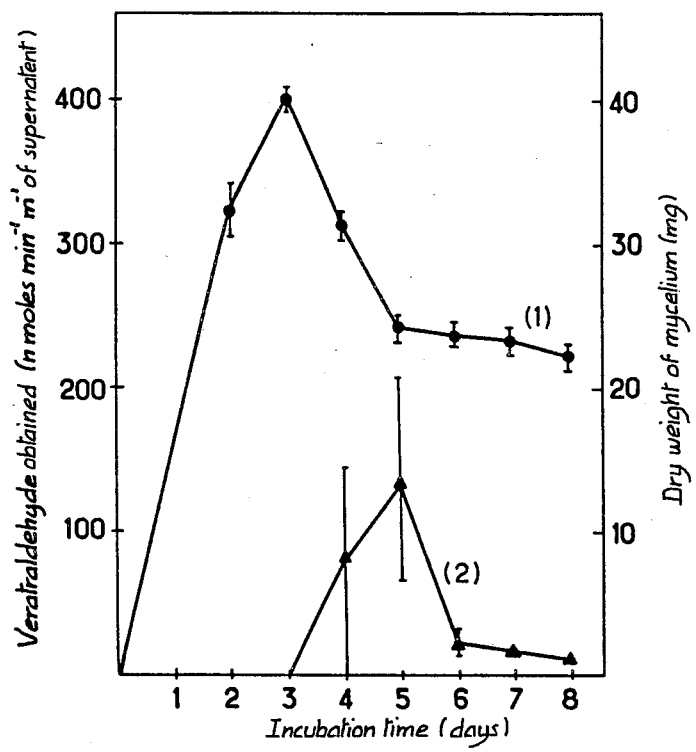
Figure 3:
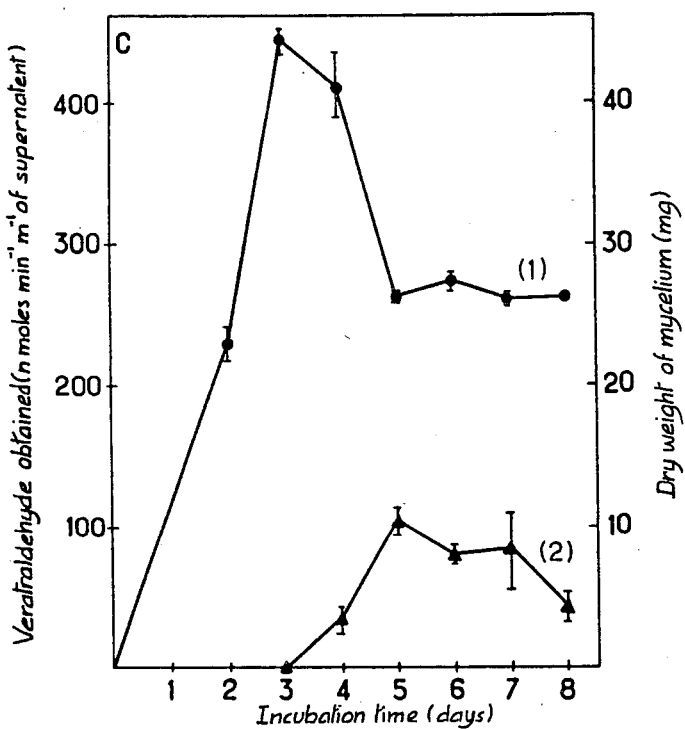
Figure 4:
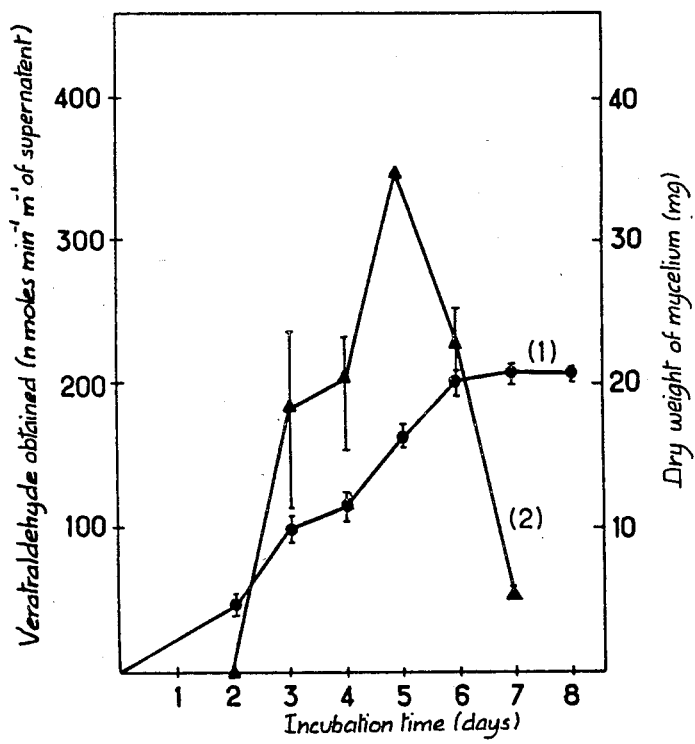

The results obtained with *P. chrysosporium* C.N.C.M.-I-398 can be found on the attached drawing, in which:

FIG. 1: curve (1) shows the effect of a deficiency of nitrogen in the culture medium (2.6 mM) on the growth of the mycelium, in the presence of glucose as the cabon source;

FIG. 2: curve (1) shows the effect of a high nitrogen content in the culture medium (26 nM) on the growth of the mycelium, in the presence of glucose as the carbon source;

FIG. 3: curve (1) shows the effect of a high nitrogen content in the culture medium (26 mM) on the growth of the mycelium, in the presence of starch as the carbon source;

FIG. 4: curve (1) shows the effect of a high nitrogen content in the culture medium (26 mM) on the growth of the mycelium, in the presence of glycerol as the carbon source.

The results show in particular that glycerol appears to be a relatively unfavorable carbon source for the growth of *P. chrysosporium* C.N.C.M.-I-398.

On glucose as the carbon source, whether or not the medium contains limited nitrogen, the growth of the mycelium is markedly greater.

By way of comparison, the growth of *P. chrysosporium* C.N.C.M.-I-398 and of a known strain, namely *P. chrysosporium* BKM-1767 (ATCC 24725), was determined in a culture medium with a high nitrogen content (26 mM), glycerol being the carbon source (initial pH of the medium: 4.5):

| Incubation time (days) | *P. chrysosporium* BKM-1767 | | *P. chrysosporium* C.N.C.M.-I-398 | |
|---|---|---|---|---|
| | Dry weight of the mycelium (mg) | pH | Dry weight of the mycelium (mg) | pH |
| 2 | 15.8 ± 1.6 | 5.46 ± 0.04 | 4.9 ± 0.4 | 5.37 ± 0.04 |
| 3 | 34.2 ± 2.6 | 4.27 ± 0.05 | 10.0 ± 1.0 | 5.05 ± 0.04 |
| 4 | 39.2 ± 3.1 | 4.08 ± 0.04 | 11.3 ± 1.5 | 5.34 ± 0.02 |
| 5 | 40.2 ± 0.7 | 4.06 ± 0.01 | 16.6 ± 0.4 | 5.33 ± 0.06 |
| 6 | 37.7 ± 1.3 | 4.17 ± 0.09 | 19.9 ± 1.0 | 4.76 ± 0.18 |
| 7 | 37.8 ± 1.3 | 4.46 ± 0.06 | 20.8 ± 0.4 | 4.45 ± 0.08 |

These results show that, under the experimental conditions, the growth of the known strain is much greater than that of *P. chrysosporium* C.N.C.M.-I-398.

It was found from later experiments that conditions of oxygenation do not influence the growth of *P. chrysosporium* C.N.C.M.-I-398, as indicated by the following results obtained from a medium containing glycerol as the carbon source and characterized by a high nitrogen content:

| Incubation time (days) | Cultures placed under a 100% oxygen atmosphere after inoculation | | Cultures placed under an air atmosphere after inoculation | |
|---|---|---|---|---|
| | Dry weight of the mycelium (mg) | pH | Dry weight of the mycelium (mg) | pH |
| 2 | 4.5 ± 1.1 | 5.22 ± 0.00 | 4.5 ± 0.2 | 5.10 ± 0.04 |
| 3 | 11.1 ± 1.3 | 5.23 ± 0.08 | 11.8 ± 3.2 | 4.97 ± 0.13 |
| 4 | 16.2 ± 2.5 | 4.97 ± 0.14 | 15.3 ± 0.9 | 5.14 ± 0.01 |
| 5 | 18.5 ± 2.4 | 5.12 ± 0.08 | 16.9 ± 3.1 | 5.11 ± 0.06 |
| 6 | 22.5 ± 4.0 | 4.35 ± 0.09 | 18.0 ± 2.5 | 5.20 ± 0.09 |
| 7 | 25.2 ± 0.5 | 4.38 ± 0.02 | 22.2 ± 1.5 | 5.14 ± 0.07 |

It was also noted in the course of these experiments that the strain *P. chrysosporium* BKM-1767 (ATCC 24725) exhibits sporulation after 5 days, which becomes intense after 6 days.

In the case of *P. chrysosporium* C.N.C.M.-I-398, a hydrophobic consistency of the mycelium and intense sporulation were observed after 5 days.

However, no sporulation was noted with *P. chrysosporium* I-399.

II. Ligninase activity

A. On a substrate for lignin-degrading enzyme

The ligninase activity of culture supernatants obtained as described in the example below was determined by measuring, at 35° C., the increase in absorbance at 310 nm due to the oxidation of veratryl alcohol (or 3,4-dimethoxybenzyl alcohol) to veratraldehyde, in accordance with the method described in Proc. Natl. Acad. Sci. U.S.A., volume 81, pages 2280–2284 (1984).

This was carried out using the same reaction mixture as the one in the reference in question, except for the hydrogen peroxide, which was used at a concentration of 0.27 mM.

The enzyme activity was defined in units, one unit corresponding to 1 nmol/minute of veratraldehyde formed under the experimental conditions.

The results obtained with *P. chrysosporium* C.N.C.M.-I-398 can be found on the attached drawing, in which:

FIG. 1: curve (2) shows the effect of a deficiency of nitrogen in the culture medium (2.6 mM) on the ligninase activity, in the presence of glucose as the carbon source;

FIG. 2: curve (2) shows the effect of a high nitrogen content in the culture medium (26 mM) on the ligninase activity, in the presence of glucose as the carbon source;

FIG. 3: curve (2) shows the effect of a high nitrogen content in the culture medium (26 mM) on the ligninase activity, in the presence of starch as the carbon source;

FIG. 4: curve (2) shows the effect of a high nitrogen content in the culture medium (26 mM) on the ligninase activity, in the presence of glycerol as the carbon source.

FIG. 1 shows that if *P. chrysosporium* C.N.C.M.-I-398 is cultivated under state-of-the-art conditions, i.e. in a medium which is deficient in nitrogen and which contains glucose as the carbon source, ligninase activity appears in the culture supernatants after 3 days.

However, the maximum value of this activity, which is of the order of 50 units after 5 days, is found to be low and comparable to the enzyme activity detected in comparative cultures of a known strain, namely *P. chrysosporium* ME-466 (ATCC 34541) (10 to 20 units).

On the other hand, FIGS. 2 and 3 show that ligninase activity is easily detectable in cultures which have a high nitrogen content (26 mM) and in which the carbon source is glucose or soluble starch.

In cultures which have a high nitrogen content and contain either glucose or starch as the carbon source, the activity is still significant 4 days after the growth of the mycelium has peaked.

In cultures which have a high nitrogen content and use glycerol as the carbon source, it is seen that the enzyme production is very greatly increased.

The activity appears between 2 and 3 days after inoculation and frequently exceeds 350 units after 5 days.

The high levels of enzyme activity observed when glycerol is the carbon source are very probably related to the low growth rate of *P. chrysosporium* C.N.C.M.-I-398 on glycerol compared with glucose.

By way of comparison, the ligninase activity obtained by the culture of *P. chrysosporium* C.N.C.M.-I-398 and of a known strain, namely *P. chrysosporium* BKM-1767 (ATCC 24725), in a culture medium with a high nitrogen content (26 mM) and glycerol content, was determined.

The following results were obtained:

| Incubation time (days) | *P. chrysosporium* BKM-1767 | *P. chrysosporium* C.N.C.M.-I-398 |
|---|---|---|
| | Units of ligninase activity/ml of medium | |
| 2 | 0 | 0 |
| 3 | 11 ± 9 | 182 ± 69 |
| 4 | 0 | 203 ± 42 |
| 5 | 2 ± 2 | 353 ± 0 |
| 6 | 3 ± 4 | 224 ± 40 |
| 7 | 1 ± 1 | 58 ± 4 |

These results again prove that the ligninase activity is produced by *P. chrysosporium* C.N.C.M.-I-398 provided that the nitrogen content of the culture medium is high, in contrast to the known *P. chrysosporium* strain.

Complementrary experiments performed under the same conditions, i.e. in a glycerol medium not deficient in nitrogen, showed ligninase activity levels of 490.7±4.5 units and 641.8±61.6 units by the culture of *P. chrysosporium* C.N.C.M.-I-398 and *P. chrysosporium* C.N.C.M.-I-399 respectively.

B. On lignin model compounds

The enzyme activity of culture supernatants obtained as described in the example below was determined.

This was done by measuring, at 35° C., the formation of 3,4,5-trimethoxybenzaldehyde due to the oxidative degradation, dependent on hydrogen peroxide, of 1-(3,4,5-trimethoxyphenyl)-2-(2,6-dimethoxy-4-hydroxymethylphenyl)propane-1,3-diol, in accordance with the method described in Proc. Natl. Acad. Sci. U.S.A., volume 81, pages 2280–2284 (1984) for the non-radioactive β-1 (diarylpropane) dimers.

Likewise, the formation of veratraldehyde due to the oxidative degradation, dependent on hydrogen peroxide, of 1-(3,4-dimethosyphenyl)-2-(2-methoxyphenoxy)-propane-1,3-diol was measured, at 35° C., according to the method also described in Proc. Natl. Acad. Sci., U.S.A., volume 81, pages 2280–2284 (1984) for the β-O-4 ether dimers (arylglycerol-aryl ether).

The results of these experiments revealed a high level of ligninase activity demonstrated by cleavage of the $C_\alpha$-$C_\beta$ bonds in the model compounds used.

It was also possible to demonstrate an important effect of the oxygen partial pressure on culture media of *P. chrysosporium* C.N.C.M.-I-398 containing glucose as the carbon source, but a less marked effect on media containing glycerol.

The cultures of this microorganism in a glucose medium not deficient in nitrogen absolutely must have a pure oxygen atmosphere if ligninase activity is to appear, whereas the cultures of the same microorganisms in a glycerol medium not deficient in nitrogen develop this activity in an air or oxygen atmosphere.

However, the levels of enzyme activity recorded in an air atmosphere were shown to be four times lower than in a pure oxygen atmosphere.

III. Lignin-degrading activity

The following tests for lignin-degrading activity were carried out using $^{14}$C-DHP as the synthetic lignin (DHP: polymer from dehydrogenation of coniferyl alcohol).

(1) Supernatants obtained after 5 days of culturing *P. chrysosporium* C.N.C.M.-I-398 as described in the example below are decanted. They are combined and 9 ml of the mixture obtained are reintroduced into the flasks containing the cultures.

0.5 ml of a 20% glucose solution (weight/volume) is then added and 0.5 unit of glucose oxidase (0.5 ml of a freshly prepared solution in distilled water) is also added so as to stimulate the reaction. 0.1 ml of a suspension of $^{14}$C-DHP (5480 dpm) is introduced, the flasks are then swept continuously with oxygen and the $^{14}$CO$_2$ formed is trapped in 4 ml of a phenethylamine/methanol/water mixture (2:1:1). 10 ml of a scintillation liquid are then added and the radioactivity is measured in a scintillation counter.

This gave the following results, expressed in % of total available $^{14}$C:

| Time (h) after initiation of the reaction | % of cumulated initial $^{14}$C (converted to $^{14}$CO$_2$) |
|---|---|
| 2.5 | 54 ± 4 |
| 5 | 65 ± 7 |
| 24 | 66 ± 7 |

These results show that culture media of *P. chrysosporium* C.N.C.M.-I-398 make it possible to cause a high level of degradation of synthetic lignin in the presence of hydrogen perioxide generated by the glucose/glucose oxidase system.

In other similar experiments, up to 79% of $^{14}$C in the form of $^{14}$CO$_2$ was obtained after 2 hours.

(2) Cultures of *P. chrysosporium* C.N.C.M.-I-398 are prepared, at 37° C., in a 250 ml flask equipped so that it can be swept with oxygen.

These cultures are prepared using media similar to the one described in the example below (glucose/2.6 mM in respect of nitrogen, and glycerol/26 mM in respect of nitrogen), to which 0.1 ml of a suspension of $^{14}$C-DHP is added.

The cultures are inoculated with approximately 2.3·10$^5$ spores, the flask is swept periodically with 100% oxygen for 2 minutes and the $^{14}$CO$_2$ formed is trapped in 4 ml of a phenethylamine/methanol/water mixture (2:1:1). 10 ml of a scintillation liquid are added and the radioactivity is measured in a scintillation counter.

This gave the following results, expressed in % of total available $^{14}$C:

| Incubation time (days) | % of cumulated initial $^{14}$C (converted to $^{14}$CO$_2$) | |
|---|---|---|
| | glucose/2.6 mM in respect of nitrogen | glycerol/26 mM in respect of nitrogen |
| 7 | 11 | 47 |
| 8 | 15 | 48 |
| 9 | 17 | 49 |
| 12 | 23 | 50 |
| 14 | 25 | 52 |

These results confirm the superiority of the preferred culture conditions according to the invention (high glycerol and nitrogen content) in terms of the degradation of synthetic lignin in a long-term experiment.

The non-limiting example which follows illustrates the invention.

EXAMPLE

Preparation of lignin-degrading enzyme (a) Culture supernatant containing lignin-degrading enzyme

*P. chrysosporium* C.N.C.M.-I-398 is kept at 4° C. on agar plates containing 2% of malt.

Also, an inoculum consisting of conidial suspensions filtered on glass wool is prepared using the sporulation medium described in Applied and Environmental Microbiology, volume 35, No. 6, pages 1223–1225 (1978).

Cultures (1% of glycerol and 26 nM in respect of nitrogen) are then prepared in 150 ml conical flasks containing 10 ml of an aqueous medium having the following composition:

| | mg |
|---|---|
| Carbon source | |
| Glycerol | 100 |
| Nitrogen source | |
| Asparagine | 10 |
| NH$_4$NO$_3$ | 5 |
| Mineral salts | |
| KH$_2$PO$_4$ | 2 |
| MgSO$_4$.7H$_2$O | 0.5 |
| CaCl$_2$.2H$_2$O | 0.132 |
| MnSO$_4$.H$_2$O | 0.05 |
| Iron citrate | 0.12 |
| ZnSO$_4$.7H$_2$O | 0.066 |
| CuSO$_4$.5H$_2$O | 0.01 |
| CoCl$_2$.6H$_2$O | 0.01 |
| Vitamin | |
| Thiamine | 0.025 |
| Yeast Extract | 1 |
| Buffer | |
| Sodium 2,2'-dimethylsuccinate | 14.6 | and the pH is adjusted to 4.5–5 with potassium hydroxide.

The cultures are inoculated with approximately 2.3·10$^5$ spores and the flasks are swept with oxygen for 2 minutes after inoculation and hermetically stoppered.

The cultures are then kept at 37° C. and a supernatant containing lignin-degrading enzyme is obtained 3 to 4 days after inoculation, the maximum enzyme activity occurring at around 5 to 6 days.

(b) Separation of lignin-degrading enzyme

The 6-day cultures are combined and centrifuged at 4° C. for 15 minutes (10,000 g). p-Methylsulfonyl fluoride (0.2 mM) is added to the supernatant in order to reduce proteolysis and the product is concentrated on a filter (pore size: 10,000 daltons) to 250 ml. Dialysis is carried out for 8 to 10 hours against a buffer solution which is 5 mM in respect of sodium tartrate (pH=4.5) and the product is introduced into a chromatography column containing agarose gel, equilibrated with the same buffer solution beforehand.

The column is washed with 100 ml of the buffer solution and a saline gradient is introduced (0-0.1M sodium chloride in a 5 mM sodium tartrate solution, pH=4.5, total volume: 400 ml).

All the purification steps are performed at 4° C. The enzyme solution is then dialyzed against deionized distilled water and the lignin-degrading enzyme is kept at −20° C. in the form of a stable lyophilized powder.

Lignin-degrading enzyme was also obtained by using the above method but replacing the glycerol with glucose or starch.

Likewise, the enzyme in question could be produced by replacing *P. chrysosporium* C.N.C.M.-I-398 with *P. chrysosporium* C.N.C.M.-I-399.

What is claimed is:

1. An essentially pure culture of *Phanerochaete chrysosporium* Burdsall strain C.N.C.M.-I-398.

2. An essentially pure culture of *Phanerochaete chrysosporium* Burdsall strain C.N.C.M.-I-399.

3. A process for producing a culture supernatant which contains lignin-degrading enzyme comprising the steps of:

cultivating a substantially pure culture of a microorganism selected from the group consisting of *Phanerochaete chrysosporium* Burdsall strain C.N.C.M.-I-398 and *Phanerochaete chrysosporium* Burdsall strain C.N.C.M.I-399 at a temperature of from 28° to 40° C. in a nutrient medium containing a source of assimilable nitrogen, assimilable carbon and assimilable mineral salts, such that the lignin-degrading enzyme is produced by the cultivated substantially pure culture of the microorganism and secreted into the nutrient medium, and separating the nutrient medium from the cultivated substantially pure culture of the microorganism, such that a culture supernatant containing lignin-degrading enzyme is obtained.

4. Process according to claim 3 in which the assimilable carbon source is selected from the group consisting of glucose, mannose, starch, melibiose, mannitol, xylose, maltose, adonitol, arabinitol, fructose, sorbitol, raffinose, xylitol, D(+)-trehalose, and glycerol.

5. Process according to claim 3 in which the assimilable carbon source is glycerol.

6. Process according to claim 3 in which the assimilable nitrogen is selected from the group consisting of asparagine, ammonium nitrate and ammonium tartrate.

7. Process according to claim 3 in which the assimilable nitrogen is selected from the group consisting of asparagine, ammonium nitrate, and mixtures thereof.

8. Process according to claim 3 in which the substantially pure microorganism culture is cultivated at 37° C.

9. A process for producing lignin-degrading enzyme comprising the steps of:

cultivating a substantially pure culture of a microorganism selected from the group consisting of *Phanerochaete chrysosporium* Burdsall strain C.N.C.M.-I-398 and *Phanerochaete chrysosporium* Burdsall strain C.N.C.M.I-399 at a temperature of from 28° to 40° C. in a nutrient medium containing a source of assimilable nitrogen, assimilable carbon and assimilable mineral salts, such that lignin-degrading enzyme accumulates in the nutrient medium, and separating the lignin-degrading enzyme from the nutrient medium by sequentially applying the techniques of centrifugation, dialysis, and chromatography.

10. Process according to claim 9 wherein the cultivated substantially pure microorganism culture and the nutrient medium which contains lignin-degrading enzyme are centrifuged at 10,000×g for 15 minutes at 4° C. such that the cultivated microorganism culture is sedimented and a culture supernatant which contains lignin-degrading enzyme is obtained.

11. Process according to claim 10 further comprising adding a proteolysis inhibitor to the culture supernatant and concentrating the culture supernatant prior to dialysis.

12. Process according to claim 11 in which the proteolysis inhibitor is p-methylsulfonyl fluoride.

13. Process according to claim 10 in which the culture supernatant is dialyzed against a buffered solution for between 8 and 10 hours.

14. Process according to claim 13 in which the buffered solution is a solution of 5 mM sodium tartrate in water, pH 4.5.

15. Process according to claim 13 in which the dialyzed culture supernatant is first applied to an agarose gel column equilibrated with a buffer and the lignin-degrading enzyme is then eluted from the agarose gel with a salt gradient.

16. Process according to claim 15 in which the buffer is a solution of 5 mM sodium tartrate in water having a pH of 4.5.

17. Process according to claim 15 in which the salt gradient is a solution of 5 mM sodium tartarte in water having a pH of 4.5 which contains sodium chloride in a graduated amount between 0 and 0.1M.

18. A method of degrading lignin comprising incubating lignin with a culture supernatant from a cultivated substantially pure culture of a microorganism selected from the group consisting of *Phanerochaete chrysosporium* Burdsall strain C.N.C.M.-I-398 and *Phanerochaete chrysosporium* Burdall strain C.N.C.M.-I-399, the culture supernatant containing lignin-degrading enzyme.

19. A method of degrading lignin comprising incubating lignin with an enzymatically effective amount of substantially pure lignin-degrading enzyme of *Phanerochaete chrysosporium* Burdsall strain C.N.C.M.-I-398.

20. A method of degrading lignin comprising incubating lignin with an enzymatically effective amount of substantially pure lignin-degrading enzyme of *Phanerochaete chrysosporium* Burdsall strain C.N.C.M.-I-399.

* * * * *